United States Patent [19]

Pischky

[11] Patent Number: 4,710,220
[45] Date of Patent: Dec. 1, 1987

[54] BIOCIDAL PASTE

[75] Inventor: Hans Pischky, Lautertal, Fed. Rep. of Germany

[73] Assignee: Ciba-Geigy Corp., Ardsley, N.Y.

[21] Appl. No.: 793,867

[22] Filed: Nov. 1, 1985

[30] Foreign Application Priority Data

Nov. 7, 1984 [CH] Switzerland ................ 5360/84

[51] Int. Cl.$^4$ ................................ A01N 25/00
[52] U.S. Cl. ............................ 71/67; 71/DIG. 1; 106/18.33
[58] Field of Search .................. 71/67, DIG. 1; 106/18.33, 15.05

[56] References Cited

U.S. PATENT DOCUMENTS 3,629,256  12/1971  Berrer et al. ............... 260/249.8
3,741,745   6/1973  Berrer et al. ............... 71/93

FOREIGN PATENT DOCUMENTS 100143  9/1973  German Democratic Rep.

Primary Examiner—Catherine L. Mills
Attorney, Agent, or Firm—Edward McC. Roberts; Harry Falber

[57] ABSTRACT

A preparation in paste form which contains an s-triazine (I) and a polyethylene glycol/polypropylene glycol condensate or an ethoxylated compound (II)

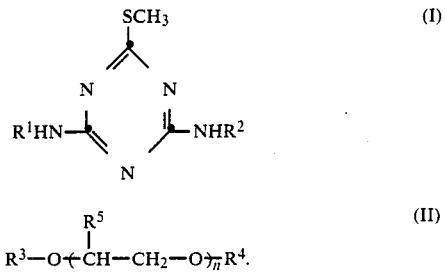

In these formulae, $R^1$ and $R^2$ are $C_2$–$C_6$-alkyl or $C_3$–$C_6$-cycloalkyl, $R^3$ and $R^4$ independently of one another are each hydrogen, alkyl, unsubstituted or substituted phenyl or a $C_6$–$C_{20}$-acyl radical, $R^5$ is hydrogen or methyl, and n is an integer between 1 and 10.

The paste is suitable as an algicide for water-containing or solvent-containing lacquer systems, especially for disperse dyes or antifouling paints.

8 Claims, No Drawings

BIOCIDAL PASTE

BIOCIDAL PASTE

The present invention relates to preparations in paste form containing s-triazines and polyethoxylated compounds, to a process for producing these preparations, and to their use as algicides.

2,6-Diamino-4-methylthio-s-triazines are known algicides or herbicides. The substances are insoluble in water, and are added, in a finely ground form, as solids to water-containing systems, whereupon there are formed suspensions, which in their turn do not have unlimited storage stability. In the DDR Patent Specification No. 100,143 are described for example herbicidally active suspensions consisting of a triazine, sulfite liquor, water and nonylphenol polyglycol ether.

Coating systems containing solvents can be treated with biocidal active substances in the dissolved form or in the paste form. There is thus known for example a paste based on tributyltin fluoride/xylene. This system can however not be used at a high concentration in aqueous or water-containing systems.

Since in general with regard to industrial hygiene problems arise from the handling of powders, preparations in paste form for use as formulation auxiliaries are particularly highly valued. In contrast to pulverulent forms of such products, those in paste form have not the tendency in storage to form lumps, and can be easily added in controlled amounts and stirred into the substrate concerned. Furthermore, no nuisance occurs as a result of the release of dust during the controlled addition. The biocidal active substance is thus simple to add and to uniformly disperse.

There is therefore a need for a biocidal paste which can be applied in both aqueous and solvent-containing lacquer systems, and which can be produced by a simple grinding of the components.

The present invention relates to preparations in paste form which contain:

(a) an s-triazine of the formula I

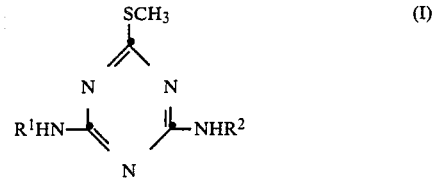

wherein $R^1$ and $R^2$ independently of one another are each $C_2$–$C_6$-alkyl or $C_3$–$C_6$-cycloalkyl, and (b) at least one polyethylene glycol/polypropylene glycol condensate or one compound of the formula II

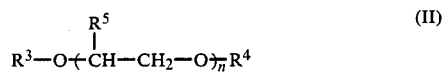

wherein $R^3$ and $R^4$ independently of one another are each a monovalent acyl radical of a saturated or unsaturated $C_6$–$C_{20}$-carboxylic acid, or are hydrogen, $C_1$–$C_{20}$-alkyl or phenyl, or phenyl substituted by one or two $C_1$–$C_{12}$-alkyl groups, and $R^5$ is hydrogen or methyl, and wherein the index n is an integer between 1 and 10, and the weight ratio of component (a) to component (b) is 30:70 to 70:30.

As $C_2$–$C_6$-alkyl, $R^1$ and $R^2$ are for example: ethyl, propyl, isopropyl, butyl, sec-butyl, pentyl, isopentyl, hexyl, 1,2-dimethylpropyl, 1,2-dimethylbutyl or 2,3-dimethylbutyl. Particularly preferred are branched-chain $C_3$–$C_6$-alkyl groups, for example isopropyl, 1,2-dimethylpropyl or tert-butyl.

As $C_3$–$C_6$-cycloalkyl, $R^1$ and $R^2$ are for example: cyclopropyl, cyclobutyl, cyclopentyl or cyclohexyl, cyclopropyl being preferred.

As a monovalent acyl radical of a $C_6$–$C_{20}$-carboxylic acid, $R^3$ and optionally $R^4$ are derived for example from: caproic acid, lauric acid, myristic acid, palmitic acid, stearic acid, arachic acid or oleic acid. Derivatives of $C_{12}$–$C_{20}$-carboxylic acids are preferred, and especially the oleic acid derivatives.

As $C_1$–$C_{20}$-alkyl, $R^3$ and optionally $R^4$ are preferably straight-chain, and are for example: methyl, ethyl, n-propyl, n-butyl, n-pentyl, n-hexyl, n-heptyl, n-octyl, n-nonyl, n-dodecyl, n-tetradecyl, n-hexadecyl, n-octadecyl or n-eicosyl. $R^4$ and/or $R^3$ are preferably straight-chain $C_8$–$C_{18}$-alkyl, and more especially straight-chain $C_{12}$–$C_{18}$-alkyl.

As phenyl substituted by $C_1$–$C_{12}$-alkyl, $R^3$ and optionally $R^4$ are for example: o-, m- or p TM methyl-, -butyl-, -hexyl-, -octyl-, -nonyl-, -decyl- or -dodecylphenyl. The p-derivatives are preferred, and in particular p-nonylphenyl. The preferred meaning of $R^3$ and optionally $R^4$ is phenyl The phenyl radicals disubstituted by $C_1$–$C_{12}$-alkyl are homologues of the monosubstituted phenyl radicals mentioned above, the alkyl radicals being for example in the 2,3-, 2,4-, 2,5-, 2,6- or 3,4-position.

Preferred s-triazines of the formula I are those wherein $R^1$ is branched-chain $C_3$–$C_6$-alkyl, for example isopropyl, 1,2-dimethylpropyl or tert-butyl; or wherein $R^1$ is cyclopropyl.

Likewise preferred are compounds of the formula I wherein $R^1$ is ethyl or cyclopropyl, and wherein $R^2$ is tert-butyl, 1,2-dimethylpropyl or isopropyl.

More especially preferred as component (b) are compounds of the formula II, particularly those compounds of the formula II wherein $R^4$ is hydrogen, and/or wherein $R^3$ is a monovalent acyl radical of a $C_{12}$–$C_{20}$-carboxylic acid.

Also of interest in the preparations according to the invention are compounds of the formula II wherein $R^5$ is hydrogen.

A particularly preferred embodiment of the paste according to the invention contains 50 to 60% by weight of 2-tert-butylamino-4-methylthio-6-cyclopropylamino-s-triazine as component (a), and 40 to 50% by weight of polyethylene glycol oleic acid ester as component (b).

The components (a) and (b) of the paste according to the invention are as a rule products obtainable commercially, or they can be produced by known methods.

More especially preferred as component (b) is the polyethylene glycol oleic acid ester which is obtainable commercially under the designation IRGASTAT ®33.

The compound of the formula II is liquid at room temperature.

The preparation according to the invention is virtually a dispersed system (dispersion). In this system, the s-triazine, as the disperse phase, is finely dispersed in a dispersant (the polyethoxylated component). The term "fine dispersion" indicates the fact that the biocide in the paste is in a form free from agglomerates.

The disperse phase is present in a finely crystalline form. The paste can be advantageously produced by a process comprising mixing the coarse-crystalline material obtained in the preparation of the triazine with the dispersant, and subsequently grinding this mixture, for example on a roller mill, in a ball mill or in a corundum-disk mill.

Preferably, the dispersant is allowed to act for several hours or days on the coarse-crystalline triazine before it is ground to a paste in the following operation. This procedure facilitates the paste-forming process considerably since, surprisingly, the impregnated triazine lumps then break down into minute particles without any great expenditure of energy. The paste can however be produced also by thorough mixing of finely-crystalline triazine with the dispersing agent, for example by means of a stirring apparatus. This operation can be performed, as in the case of forming the paste in a mill, at an elevated temperature, the temperature being governed in general by the viscosity of the dispersant.

The present invention thus relates also to a process for producing a preparation in paste form, which process comprises grinding a triazine of the formula I, as defined above, with a polyethylene glycol/polypropylene glycol condensate, or with a compound of the formula II as defined above, the ratio of triazine to the polyethoxylated component being 30:70 to 70:30.

Before producing the paste, it is advantageous to dry the triazine in a vessel, for example in an agitator vessel, in which subsequently the formation of the paste is effected. The procedure can however be such that the product still moist from a preceding treatment, in consequence of adhering liquid, is processed directly into a paste, and this then subjected to some form of drying and purifying treatment whereby—for example by a stirring of the paste in vacuo at a temperature of up to 100° C., or with the aid of a degassing cascade—the moisture or residues of volatile by-products of the synthesis are removed. With use of a procedure of this kind—extending namely from the synthesis of the triazine, through the subsequent production and storage of the paste and right up to its incorporation into the substrate concerned—it is ensured that the possibility of persons being inconvenienced in any way is excluded with certainty.

The pastes according to the invention are applied in all cases where substrates, or if necessary objects, are to be protected against the growth of algae or diatoms. These substrates are for example disperse dyes, antifouling paints or paints containing solvents. They can however also be plastic dispersions.

A particular advantage of the pastes according to the invention is their applicability in both water-containing and solvent-containing systems.

The pastes are easy to introduce in controlled amounts, and can be dispersed without difficulty by being stirred into the substrate concerned.

Depending on the purpose of application, the triazine paste is used in the concentration ranges known to a person skilled in the art. The limits of the normal concentrations are as follows: whereas in water, for example cooling water or in water tanks, concentrations in the ppm range suffice, in paints or coating materials concentrations of up to 60% by weight are customary.

The triazine paste optionally contains further additives, for example wetting agents or emulsifiers, which result in the formation of homogeneous dispersions, and thus ensure in the formed paste and subsequently in the given substrate a good dispersion of the triazine. Additional biocides are preferably added. In the case of antifouling paints, a combination with a biocide which is effective against animal growth organisms has proved advantageous. Also applicable are for example: metallic copper(powder), $Cu_2O$, zinc oxide, triorganotin compounds, such as tributyltin oxide, tributyltin fluoride or triphenyltin chloride; or in general substances which are known to a person skilled in the art as being effective against animal growth organisms. The combination with a fungicide is appropriate in disperse dyes and (plaster) coatings. In the treatment of water, it is preferable to have a combination with a bactericide in order to combat muciferous bacteria, whilst the triazine active substance is active in particular against muciferous algae. A combination also with further algicides is in many cases of advantage.

Customary basic substances for antifouling paints are the lacquer raw materials designated as binders and known to the expert, such as natural and synthetic resins, homo- and copolymeric products with monomeric vinyl chloride, vinylidene chloride, styrene, vinyltoluene, vinyl esters, acrylic acid and methacrylic acid, and also esters thereof, also chlorinated rubber, natural and synthetic rubber, optionally chlorinated or cyclised, also reaction resins, such as epoxide resins, polymethanes or unsaturated polyesters which, if required, can be converted by the addition of curing agents into film-forming, higher-molecular products.

A particularly preferred field of application is that of protective coatings, especially antifouling paints, as well as disperse paints or disperse plaster coatings, which contain, besides the customary basic materials and additives, 0.3 to 60% by weight, preferably 0.3 to 25% by weight, relative to the total mixture, of the triazine paste according to the invention, or a mixture of these pastes.

The invention relates also to the use of the above-defined triazine paste in solvent- or water-containing substrates which are to be protected against the growth of algae or diatoms.

The substrates which have been treated with the paste according to the invention can in their turn be used as effective agents against fresh-water and sea-water algae and diatoms.

There can be protected with the aforementioned substrates in general all materials which come into contact with water, which contain water and which are susceptible to the growth of algae, or in the case of which the growth of algae is promoted by moisture, for example from the atmosphere. These materials include for example: wood, cellulose, textiles, leather, optical glass and other forms of glass, plastics, rubber, adhesives, concrete or other building materials, and also metal components.

EXAMPLES 1. 60 g of 2-tert-butylamino-4-methylthio-6-cyclopropyl-amino-s-triazine (IRGASAFE ® 1051) in granular form and 40 g of polyethylene glycol oleic acid ester (IRGASTAT ® 33) are stirred up together, and are allowed to react for 12 hours. During this time, the granulate softens, and can be subsequently crushed in a mortar with the pestle. The crushed substance is afterwards ground down in a double pass on a laboratory ointment three-roll mill to thus obtain a homogeneous, cream-coloured paste. 2.-5. As in the preceding Example, there are used 60 g of IRGASAFE ® 1051 (granular form) and in each case 40 g of an ethoxylated component listed in the following Table. The pre-softening time is 2 days, and in each test are obtained pastes having a particle size of between 10 and 40 μm. The size of the triazine particles is dependent on the gap width of the ointment roll mill used to produce the paste.

TABLE

| Example No. | Type of compound | Trade name |
|---|---|---|
| 2 | polyethylene glycol | Polyethylene glycol 400 |
| 3 | mono-/dimethylphenol-polyglycol ether | Marlophen ® X |
| 4 | ethoxylated phenol | Marlophen ® P |
| 5 | polyethylene glycol/polypropylene glycol ether | — |

6. IRGASAFE ® 1051 and IRGASTAT ® 33 are processed in varying mixture ratios into pastes by the process described in Example 1. Products having different consistency values are obtained. The results are summarised in the following Table.

TABLE

| Concentration of triazine (% by weight) | Concentration of polyethylene glycol component (% by weight) | Consistency of the paste |
|---|---|---|
| 70 | 30 | very solid; nature of a very solid vaseline |
| 60 | 40 | solid; still not flowing |
| 50 | 50 | just flowable |
| 40 | 60 | flowable |
| 30 | 70 | flowable |

7. Affect of the porosity of the triazine granulate on the paste-forming process IRGASAFE ® 1051 is melted down over a flame. There is thus formed a golden-yellow, transparent melt which, after cooling, retains the shade of colour and the clear appearance, but which solidifies to form a solid lump. This lump is broken up by a blow with a porcelain pestle, so that nothing but small crystals remain, and these are taken up with IRGASTAT ® 33. After a reaction time of two days, the behaviour of the substrate with regard to processing properties is the same as that of specimens which have been produced from the granulated material.

What is claimed is:

1. A water-free algicide preparation in paste form which consists essentially of:
   (a) an s-triazine of the formula I

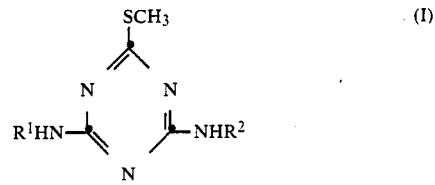

wherein $R^1$ and $R^2$ independently of one another are each $C_2$-$C_6$-alkyl or $C_3$-$C_6$-cycloalkyl, and
   (b) at least one polyethylene glycol/polypropylene glycol condensate or one compound of the formula II

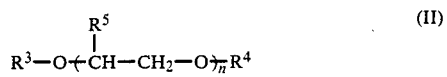

wherein $R^3$ and $R^4$ independently of one another are each a monovalent acyl radical of a saturated or unsaturated $C_6$-$C_{20}$-carboxylic acid, or are hydrogen, $C_1$-$C_{20}$-alkyl or phenyl, or phenyl substituted by one or two $C_1$-$C_{12}$-alkyl groups, and $R^5$ is hydrogen or methyl, and wherein the index n is an integer between 1 and 10, and the weight ratio of component (a) to component (b) is 30:70 to 70:30.

2. A preparation in paste form according to claim 1, wherein $R^1$ is branched-chain $C_3$-$C_6$-alkyl or cyclopropyl.

3. A preparation in paste form according to claim 1, wherein $R^1$ is ethyl or cyclopropyl, and $R^2$ is tert-butyl, 1,2-dimethylpropyl or isopropyl.

4. A preparation in paste form according to claim 2, which contains as component (b) a compound of the formula II.

5. A preparation in paste form according to claim 4, wherein $R^4$ is hydrogen.

6. A preparation in paste form according to claim 4, wherein $R^3$ is a monovalent acyl radical of a $C_{12}$-$C_{20}$-carboxylic acid.

7. A preparation in paste form according to claim 4, wherein $R^5$ is hydrogen.

8. A method of combatting algae in dispersed dyes, lacquers or antifouling paints which comprises incorporating therein an effective algae combatting amount of a preparation according to claim 1.

* * * * *